(12) United States Patent
Kent et al.

(10) Patent No.: US 8,240,020 B2
(45) Date of Patent: Aug. 14, 2012

(54) STENT RETENTION MOLD AND METHOD

(75) Inventors: Darrin J. Kent, Murrieta, CA (US);
Boyd V. Knott, Menifee, CA (US);
Jeremy L. Stigall, Murrieta, CA (US);
Kyle M. Krueger, Carlsbad, CA (US);
Sean A. McNiven, Del Mar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1461 days.

(21) Appl. No.: 11/479,048

(22) Filed: Jun. 30, 2006

(65) Prior Publication Data
US 2008/0001328 A1    Jan. 3, 2008

(51) Int. Cl.
*B23P 11/02* (2006.01)
*B21D 39/00* (2006.01)
*B29C 49/00* (2006.01)

(52) U.S. Cl. .......................... 29/447; 29/522.1; 425/522

(58) Field of Classification Search ............... 29/447, 29/428, 464, 522.1, 523; 425/522, 392, 393, 425/470, 403
See application file for complete search history.

(56) References Cited

U.S. PATENT DOCUMENTS

| | | | | |
|---|---|---|---|---|
| 4,130,617 A * | 12/1978 | Wallace | ........................ | 264/528 |
| 4,264,294 A * | 4/1981 | Ruiz | ............................. | 425/466 |
| 5,630,830 A * | 5/1997 | Verbeek | ........................ | 606/198 |
| 5,653,691 A * | 8/1997 | Rupp et al. | ............... | 604/103.06 |
| 5,672,169 A * | 9/1997 | Verbeek | ............................. | 606/1 |
| 5,759,474 A * | 6/1998 | Rupp et al. | ..................... | 264/496 |
| 6,077,273 A * | 6/2000 | Euteneuer et al. | ............. | 606/108 |
| 6,290,485 B1 * | 9/2001 | Wang | .............................. | 425/470 |
| 6,387,117 B1 * | 5/2002 | Arnold et al. | .................. | 623/1.1 |
| 6,464,720 B2 * | 10/2002 | Boatman et al. | ............. | 623/1.15 |
| 6,481,262 B2 * | 11/2002 | Ching et al. | ..................... | 72/416 |
| 6,540,774 B1 * | 4/2003 | Cox | ............... | 623/1.15 |
| 6,561,788 B1 * | 5/2003 | Gaudoin | ........................ | 425/522 |
| 6,569,193 B1 * | 5/2003 | Cox et al. | ..................... | 623/1.15 |
| 6,676,697 B1 * | 1/2004 | Richter | ........................ | 623/1.16 |
| 6,726,713 B2 * | 4/2004 | Schaldach et al. | ........... | 623/1.11 |
| 6,776,604 B1 * | 8/2004 | Chobotov et al. | ............. | 425/522 |
| 6,911,041 B1 * | 6/2005 | Zscheeg | ........................ | 623/1.15 |
| 6,948,223 B2 * | 9/2005 | Shortt | ............................. | 29/272 |
| 7,055,237 B2 * | 6/2006 | Thomas | ........................ | 29/458 |
| 7,097,440 B2 * | 8/2006 | Papp et al. | ..................... | 425/112 |

(Continued)

FOREIGN PATENT DOCUMENTS

DE    19746882    4/1999

(Continued)

OTHER PUBLICATIONS

U.S. Appl. No. 10/879,328, filed Jun. 28, 2004, Gale et al.

(Continued)

*Primary Examiner* — David Angwin
(74) *Attorney, Agent, or Firm* — Squire Sanders (US) LLP

(57) ABSTRACT

A stent retention mold includes two half-molds, each half-mold including a stent supporting surface, and a plurality of protrusions disposed on at least one of the stent supporting surfaces. A stent retention method includes retaining a stent to a balloon using a split mold that includes a stent supporting surface having a plurality of protrusions, so that a portion of the balloon extends through a gap of the stent into a space between two protrusions.

24 Claims, 4 Drawing Sheets

U.S. PATENT DOCUMENTS

| | | | |
|---|---|---|---|
| 7,381,048 B2 * | 6/2008 | Brown et al. ............... 425/522 |
| 7,708,548 B2 * | 5/2010 | Brown et al. ............... 425/522 |
| 2002/0077690 A1 | 6/2002 | Wang |
| 2002/0099406 A1 | 7/2002 | St. Germain |
| 2003/0208254 A1 | 11/2003 | Shortt |
| 2004/0236405 A1 * | 11/2004 | Kula et al. ............... 623/1.15 |
| 2004/0249435 A1 | 12/2004 | Andreas |

FOREIGN PATENT DOCUMENTS

| | | |
|---|---|---|
| WO | WO 97/40780 | 11/1997 |
| WO | WO 00/49973 | 8/2000 |
| WO | WO 02/053066 | 7/2002 |
| WO | WO 02/066095 | 8/2002 |

OTHER PUBLICATIONS

U.S. Appl. No. 10/956,759, filed Sep. 30, 2004, Durcan.
U.S. Appl. No. 10/956,910, filed Sep. 30, 2004, Huang et al.
U.S. Appl. No. 10/956,911, filed Sep. 30, 2004, Durcan.
U.S. Appl. No. 12/772,893, filed May 3, 2010, Brown et al.
International Search Report for PCT/US2006/012872, mailed Jan. 15, 2007, 18 pgs.
International Search Report for PCT/US2007/015421 filed Jun. 29, 2007, mailed Dec. 14, 2007, 12 pgs.

* cited by examiner

STENT RETENTION MOLD AND METHOD

FIELD OF THE INVENTION

This invention relates to a mold for stent retention, in particular a split mold for stent retention, and a method for stent retention.

BACKGROUND

A typical stent is a cylindrically shaped device, which holds open and sometimes expands a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty. "Restenosis" refers to the reoccurrence of stenosis in a blood vessel or heart valve after it has been subjected to angioplasty or valvuloplasty.

A stent is typically composed of scaffolding that includes a pattern or network of interconnecting structural elements often referred to in the art as struts or bar arms. The scaffolding can be formed from wires, tubes, or sheets of material rolled into a cylindrical shape.

In the case of a balloon expandable stent, the stent is mounted on a balloon connected to a catheter. Mounting the stent on the balloon typically is a two-step process. First, the stent is compressed or crimped onto the balloon. Second, the compressed or crimped stent is retained or secured on the balloon. The retained stent should have a sufficiently small diameter so that it can be transported through the narrow passages of blood vessels. The stent must be secured on the balloon during delivery until it is deployed at an implant or treatment site within a vessel in the body of a patient. The stent is then expanded by inflating the balloon. "Delivery" refers to introducing and transporting the crimped stent through a bodily lumen to the treatment site in a vessel. "Deployment" corresponds to the expanding of the crimped stent within the lumen at the treatment site. Delivery and deployment of a stent are accomplished by positioning the stent about one end of a catheter, inserting the end of the catheter through the skin into a bodily lumen, advancing the catheter in the bodily lumen to a desired treatment location, inflating the stent at the treatment location, and removing the catheter from the lumen by deflating the balloon.

The stent should be firmly secured to the balloon to avoid detachment of the stent before it is delivered and deployed in the lumen of the patient. Detachment of a stent from the balloon during delivery and deployment can result in medical complications. A lost stent can act as an embolus that can create a thrombosis and require surgical intervention. For this reason, a stent must be securely attached to the catheter. Stent retention is greatly facilitated by protrusion of the balloon into the interstitial spaces or gaps between stent struts in a stent pattern. Preferably, a portion of a balloon extends from the interior of the stent through a stent gap to the exterior of the stent. In other words, the portion of the balloon preferably extends beyond the outer surface of the stent.

One method of retaining or securing a stent on a balloon is to use a split mold. The split mold includes two half-molds that together form a cylindrical chamber for accommodating the stent and balloon. The split mold can be opened by separating the half-molds from each other so that the stent and balloon can be placed in the chamber. Then the half-molds can be pressed together to secure the stent and balloon in the chamber. Next, the balloon is inflated with a pressurized gas to press portions of the balloon into the spaces or gaps between stent struts to retain the stent on the balloon.

A disadvantage of the conventional split mold is that the balloon cannot extend through the gaps of the stent and beyond the outer surface of the stent. The cylindrical chamber's surface, which supports the stent during balloon inflation, presses against the outer surface of the stent when the balloon is inflated, preventing the balloon from extending beyond the outer surface of the stent to enhance stent retention.

SUMMARY

The present invention overcomes the above disadvantage of the conventional split mold. The present invention provides protrusions on the stent supporting surfaces of a split mold, which allow the balloon to extend through the gaps of the stent and beyond the outer surface of the stent to enhance stent retention.

According to a first aspect of the invention, a stent retention mold includes two half-molds, each half-mold including a stent supporting surface, and a plurality of protrusions disposed on at least one of the stent supporting surfaces.

According to a second aspect of the invention, a stent retention method includes retaining a stent to a balloon using a split mold that includes a stent supporting surface having a plurality of protrusions, so that a portion of the balloon extends through a gap of the stent into a space between two protrusions on the stent supporting surface. The step of retaining may include inflating the balloon to press the portion of the balloon through the gap of the stent into the space between two protrusions on the stent supporting surface. Before the balloon is inflated, it may be desirable to align a protrusion pattern of the split mold with a strut pattern of the stent.

The stent retention method may also include placing the stent between the two half-molds. The method may additionally include separating the half-molds from each other and removing the retained stent from the split mold.

In one embodiment according to the first or second aspect of the invention, the protrusions may include a plurality of islands. Preferably, each island is less than or equal to 3 mm in length.

In another embodiment according to the first or second aspect of the invention, the protrusions may include a plurality of circumferential rings. Preferably, each ring is less than or equal to 0.5 mm in width.

In a further embodiment according to the first or second aspect of the invention, the protrusions may include a plurality of longitudinal ridges. Preferably, each ridge is less than or equal to 0.5 mm in width.

In a still further embodiment according to the first or second aspect of the invention, the protrusions may form a pattern that matches at least a portion of the strut pattern of a stent to be retained. Preferably, the width of each ridge is less than or equal to two times of the width of a stent strut.

DETAILED DESCRIPTION OF THE INVENTION

Those of ordinary skill in the art will realize that the following description of the invention is illustrative only and not in any way limiting. Other embodiments of the invention will readily suggest themselves to such skilled persons based on the disclosure herein. All such embodiments are within the scope of this invention.

Figure 1:
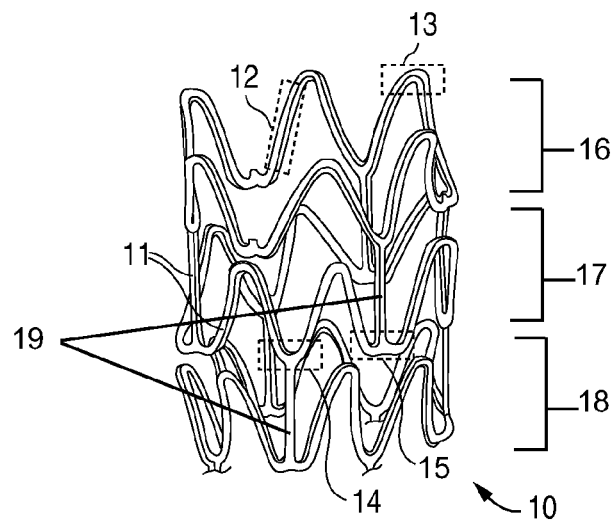
FIG. 1 shows a perspective view of a stent.

FIG. 1 illustrates a stent 10 that includes a number of interconnecting structural elements or stent struts 11. In general, the pattern of the stent struts is designed so that the stent can be radially compressed and expanded. The stent may include stent struts that are straight or relatively straight, an example being a straight portion designated by reference numeral 12. The stent may also include portions that are bent, such as the portions designated by reference numerals 13, 14, and 15. The bent portions 13, 14, and 15 may bend further when the stent 10 is crimped radially inwardly. The bent portions 13, 14, and 15 may bend less when the stent 10 is expanded radially outwardly. Stent 10 includes a plurality of undulating rings 16, 17, and 18, each of which include a plurality of stent struts and bent portions. Undulating rings 16, 17, and 18 are connected to each other by linking stent struts 19. In some embodiments, a stent may be fabricated by laser cutting a strut pattern on a tube. In other embodiments, chemical etching may be used to form a strut pattern on a tube.

The stent, as fabricated, is uncrimped and may have an outside diameter that is typically from about 1 mm and to about 4 mm. When a stent is crimped, the structural elements deform allowing the stent to decrease in diameter. The deformation occurs primarily at the bending elements. The balloon, when mounted on a catheter, may have an outside diameter of between about 0.7 mm and 0.8 mm. An outside diameter of a crimped stent may be approximately the same as the outside diameter of the balloon.

A stent can be made from one or more suitable materials. For example, a stent may be made from a metallic material. Alternatively, a stent may be made from a polymeric material. A stent material may be biostable, bioabsorbable, biodegradable or bioerodable.

Figure 2:
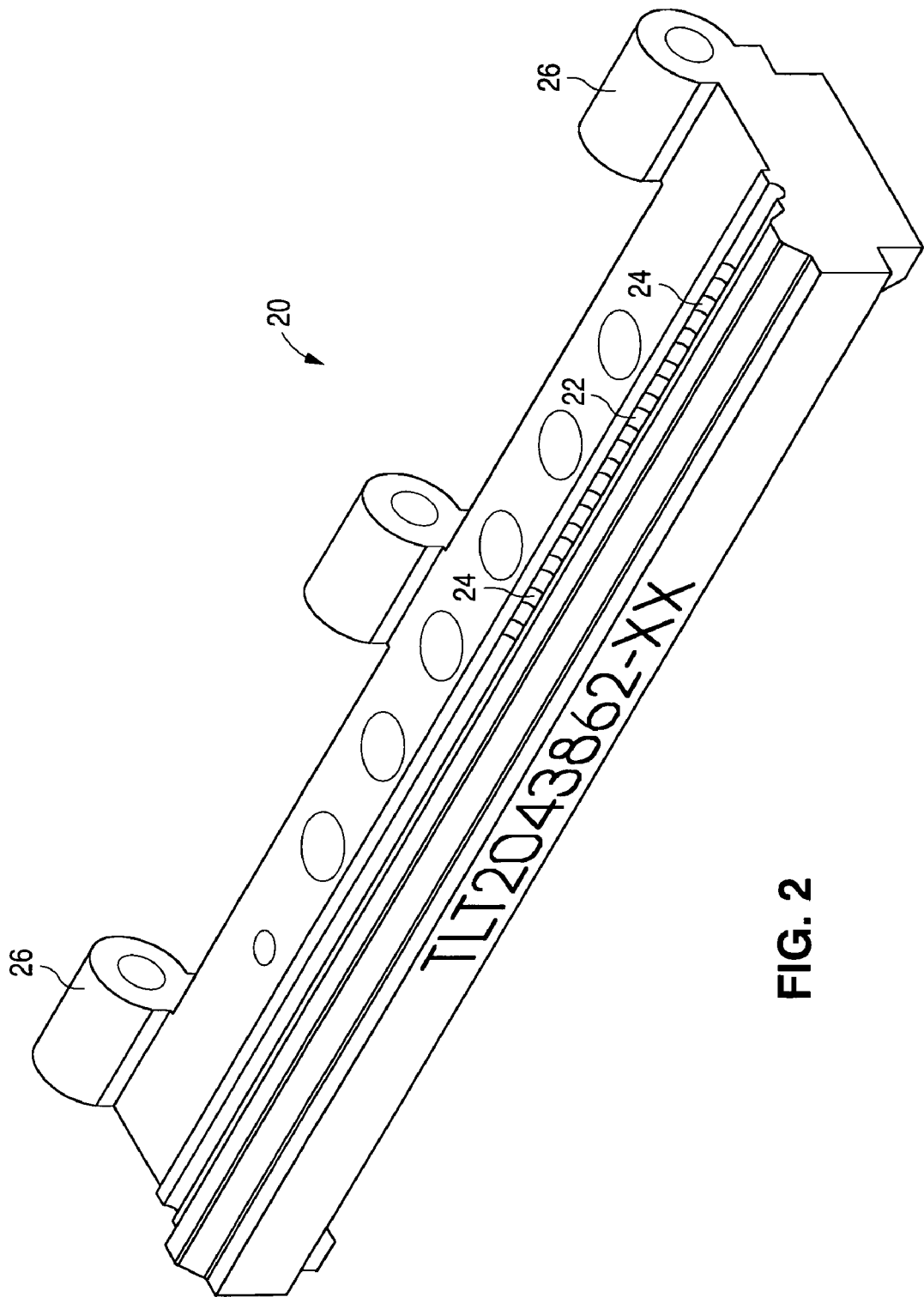
FIG. 2 shows a perspective view of a half-mold with ring-shaped protrusions.

In an embodiment of the present invention, a split mold for retaining a stent to a balloon includes two half-molds. FIG. 2 illustrates one of the half-molds. The other half-mold may be substantially a mirror image of the illustrated half-mold and therefore is not illustrated. The two half-molds together may form a cylindrical chamber for supporting the stent during stent retention. The split mold can be opened by separating the half-molds from each other so that the stent and balloon can be placed in or removed from the chamber.

The half-mold 20 shown in FIG. 2 includes a stent supporting surface 22 and a plurality of protrusions 24 disposed on the stent supporting surface 22. The half-mold 20 may also include hinges 26 so that the two half-molds can be hinged together. When the balloon is inflated, the stent supporting surfaces of the half-molds press against the outer surface of the stent to support the stent. The diameter of the stent supporting surfaces preferably is substantially equal to or slightly larger than the diameter of the crimped stent.

The protrusions 24 on the stent supporting surface 22 are circumferential rings 24 arranged along the longitudinal axis of the stent supporting surface 22. Preferably, the space between two adjacent rings 24 is sufficiently large to accommodate the portion of the balloon protruding beyond the outer surface of the stent. Since the space is defined by the height of the rings 24 and the distance between two adjacent rings 24, the height and distance preferably are sufficiently large to accommodate a protruding portion of the balloon. In some embodiments, the height of the rings 24 may be equal to or less than 0.1 mm, equal to or less than 0.3 mm, or equal to or less than 0.5 mm. The distance between two adjacent rings 24 may be between the width of the ring and 2 mm. Each ring 24 may have any suitable cross-section. For example, the cross-section of the rings 24 may be semicircular, square, or rectangular.

Figure 3:
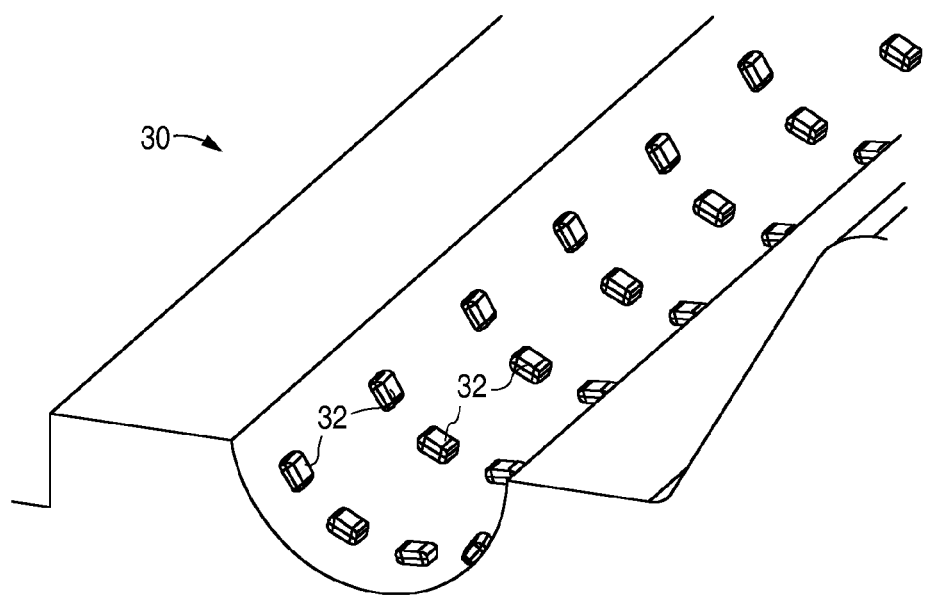
FIG. 3 shows a partial perspective view of a half-mold with island protrusions.

FIG. 3 illustrates another half-mode 30, wherein the protrusions are a plurality of islands 32. Although the illustrated islands 32 have a generally square configuration, an island may have any suitable configuration, such as a circular or rectangular configuration. In some embodiments, the width of each island 32 may be less or equal to 1 mm, less than or equal to 3 mm, or less than or equal to 5 mm. The height of the islands 32 may be equal to or less than 0.1 mm, equal to or less than 0.3 mm, or equal to or less than 0.5 mm. Preferably, the islands 32 are evenly spaced longitudinally or circumferentially, or both longitudinally and circumferentially. The distance between two adjacent islands 32 may be between one half of the island's width and two times of the island's width, between three quarters of the island's width and one and half times of the island's width, or about the island's width.

Figure 4:
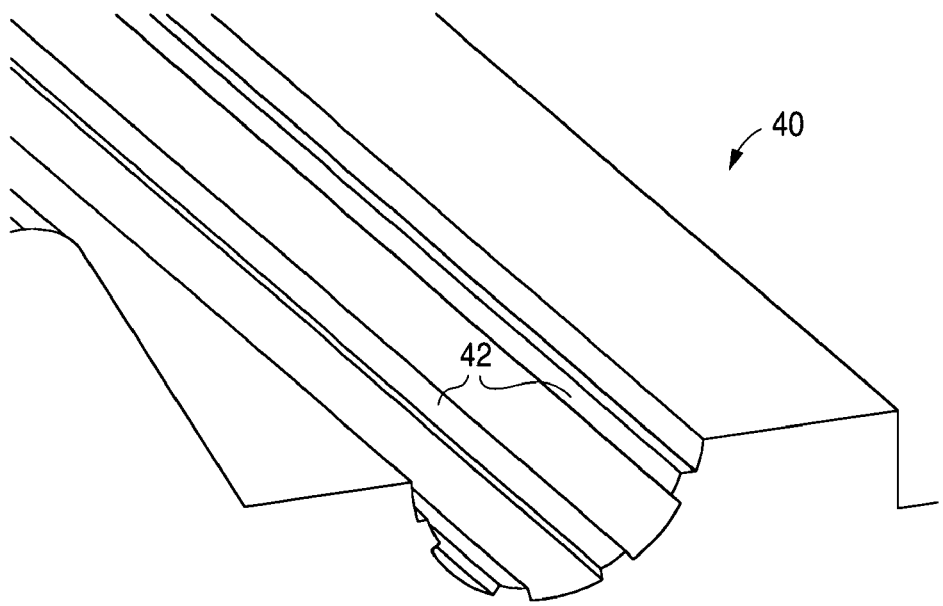
FIG. 4 shows a partial perspective view of a half-mold with longitudinal ridges.

FIG. 4 illustrates another half-mode 40, wherein the protrusions are a plurality of longitudinal ridges 42. The width of each ridge 42 may be less or equal to 1 mm, less than or equal to 3 mm, or less than or equal to 5 mm. The height of each ridge 42 may be equal to or less than 0.1 mm, equal to or less than 0.3 mm, or equal to or less than 0.5 mm. The total number of ridges may be from 3 to 20, from 5 to 15, or from 7 to 12.

Figure 5:
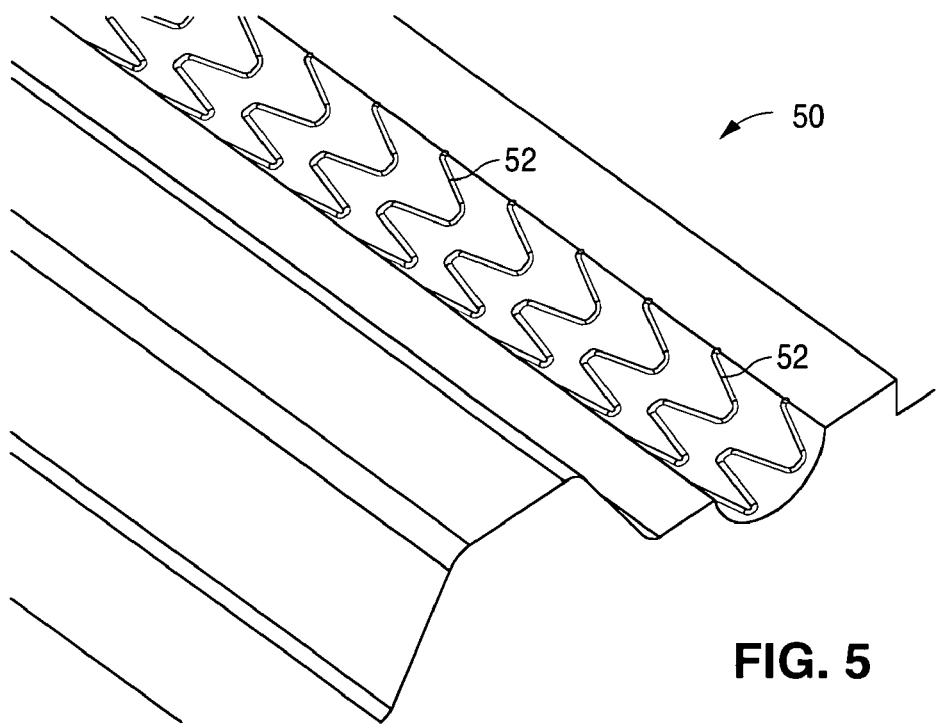
FIG. 5 shows a partial perspective view of a half-mold with protrusions that form a pattern that matches at least a portion of the strut pattern of a stent to be retained.

FIG. 5 illustrates another half-mode 50, wherein the protrusions 52 form a pattern that matches at least a portion of the strut pattern of a stent. The width of the protrusions 52 may be less or equal to one half of the strut width, less than or equal to the strut width, or less than or equal to two times of the strut width. The height of the protrusions 52 may be equal to or less than 0.1 mm, equal to or less than 0.3 mm, or equal to or less than 0.5 mm.

Figure 6:
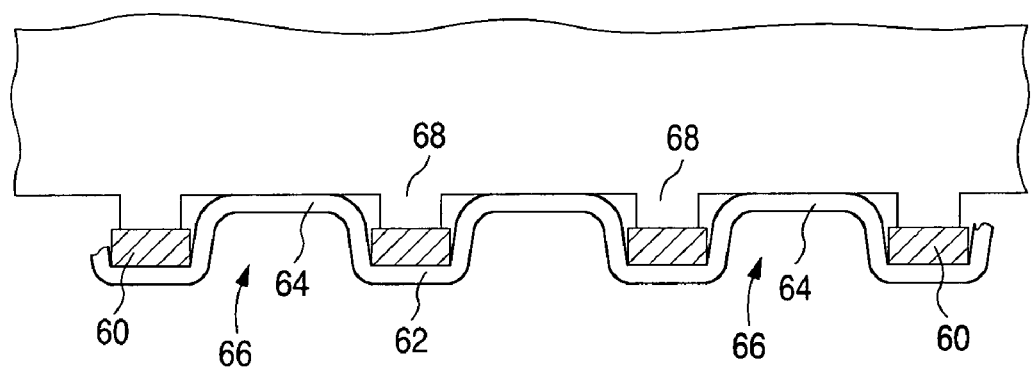
FIG. 6 shows portions of a balloon extending through the gaps of a stent, beyond the outer surface of the stent, and into the spaces between two protrusions on the stent supporting surfaces of a split mold.

To use a split mode of the present invention to retain a stent to a balloon, a crimped stent mounted on a balloon is first placed between the stent supporting surfaces of the split mold. The protrusion pattern of the split mold may be aligned with the strut pattern of the stent. The half-molds of the split mold are then pressed against each other to form a chamber to contain the stent and balloon. Then the balloon is inflated with a pressurized gas to press portions of the balloon through the gaps of the stent, beyond the outer surface of the stent, and into the spaces between two protrusions on the stent supporting surfaces. As shown in FIG. 6, when the stent 60 is properly retained on the balloon 62, certain portions 64 of the balloon 62 extend through the gaps 66 of the stent 60, beyond the outer surface of the stent 60, and into the spaces between two protrusions 68 on the stent supporting surfaces. When the balloon is being inflated, it may also be heated to enhance the pliability of the balloon. After the stent has been retained on the balloon, the half-molds can be separated from each other, and the stent and balloon can be removed from the split mold.

While particular embodiments of the present invention have been shown and described, it will be obvious to those skilled in the art that changes and modifications can be made without departing from this invention in its broader aspects.

What is claimed is:

1. A method of stent retention, comprising:
   fastening a stent to a balloon using a split mold that includes a stent supporting surface having a plurality of protrusions,
   wherein the stent comprises a plurality of interconnected stent struts including a first stent strut and a second stent strut immediately adjacent the first stent strut, the plurality of protrusions includes a first protrusion and a second protrusion, and
   wherein during the fastening step, the first protrusion directly contacts the first stent strut, the second protrusion directly contacts the second stent strut, and a portion of the balloon moves through a gap bounded by the first stent strut and the second stent strut, and moves into a space between the first protrusion and the second protrusion.

2. The method of claim 1 wherein fastening includes inflating the balloon to force the portion of the balloon through the gap between the first stent strut and the second stent strut, and into the space between the first protrusion and the second protrusion.

3. The method of claim 2 further comprising heating the balloon to assist the portion of the balloon to move into the space between the first protrusion and the second protrusion.

4. The method of claim 1 further comprising pressurizing the balloon to move the portion of the balloon into the space between the first protrusion and the second protrusion.

5. The method of claim 4 further comprising heating the balloon to assist the portion of the balloon to move into the space between the first protrusion and the second protrusion.

6. The method of claim 2 further comprising placing the stent between halves of the split mold.

7. The method of claim 6 further comprising, after the fastening step, separating the halves of the split mold from each other and removing the stent from the split mold.

8. The method of claim 1 further comprising placing the stent into the split mold and, after the fastening step, removing the stent from the split mold.

9. The method of claim 1 wherein the protrusions include a plurality of islands.

10. The method of claim 9 wherein each island is less than or equal to 3 mm in length.

11. The method of claim 1 wherein the protrusions include a plurality of circumferential rings.

12. The method of claim 1 wherein each ring is less than or equal to 0.5 mm in width.

13. The method of claim 1 wherein the protrusions include a plurality of longitudinal ridges.

14. The method of claim 13 wherein each ridge is less than or equal to 0.5 mm in width.

15. The method of claim 1 wherein the protrusions form a pattern of ridges that matches at least a portion of a strut pattern of the interconnected stent struts.

16. The method of claim 15 wherein the width of each ridge is less than or equal to two times the width of a strut of the stent.

17. The method of claim 1 further comprising aligning a protrusion pattern of the split mold with a strut pattern of the interconnected stent struts.

18. The method of claim 1, wherein using the split mold includes allowing the portion of the balloon to move through the gap, into the space, and beyond an outer surface of the stent.

19. The method of claim 1, wherein fastening the stent to the balloon includes placing an outer surface of the stent and the protrusions of the split mold into contact with each other.

20. The method of claim 19, wherein, after placing the stent and the protrusions into contact with each other, a plurality of gaps between struts of the stent are aligned with a plurality of spaces between the protrusions.

21. The method of claim 20, wherein fastening the stent to the balloon includes allowing portions of the balloon to move through the gaps and into the spaces.

22. The method of claim 21, wherein the portions of the balloon in the spaces extend radially beyond the outer surface of the stent.

23. The method of claim 1, wherein the plurality of interconnected stent struts forms a first undulating ring and a second undulating ring connected to the first undulating ring, the first stent strut is located on the first undulating ring, and the second stent strut is located on the second undulating ring.

24. The method of claim 1, wherein the plurality of interconnected stent struts forms a first undulating ring and a second undulating ring connected to the first undulating ring, and the first stent strut and the second stent strut are located on the first undulating ring.

* * * * *